United States Patent [19]

Fussi et al.

[11] Patent Number: 4,757,057
[45] Date of Patent: Jul. 12, 1988

[54] OLIGO-HETEROPOLYSACCHARIDES HAVING A HEPARIN-LIKE ACTIVITY METHOD FOR THEIR PREPARATION AND PHARMACEUTICAL COMPOSITIONS BASED THEREON

[75] Inventors: Fernando Fussi, Lesmo; Gianfranco Fedeli, Milan, both of Italy

[73] Assignee: Hepar Chimie S.A., Switzerland

[21] Appl. No.: 816,838

[22] Filed: Jan. 7, 1986

Related U.S. Application Data

[63] Continuation of Ser. No. 347,026, Feb. 8, 1982, abandoned, which is a continuation of Ser. No. 931,295, Aug. 4, 1978, abandoned.

[30] Foreign Application Priority Data

Aug. 9, 1977 [IT] Italy .............................. 26608 A/77

[51] Int. Cl.$^4$ ............................................ A61K 31/725
[52] U.S. Cl. ........................................ 514/56; 514/54
[58] Field of Search ............................................ 514/56

[56] References Cited

U.S. PATENT DOCUMENTS 2,832,766  4/1952  Wolfrom ............................ 260/211
3,585,184  12/1967  Wolfrom et al. .................... 260/209

FOREIGN PATENT DOCUMENTS 968752  3/1958  Fed. Rep. of Germany .
1032731  6/1958  Fed. Rep. of Germany .
674607  6/1952  United Kingdom ................ 424/183

OTHER PUBLICATIONS

Hladovec et al-*Experientia*, vol. XIII/5, May 15, 1957, pp. 190 & 191.
*Thrombosis Research*, vol. 9, pp. 575–583, 1976; vol. 12, 257–271 (1978); vol. 12, pp. 27–36, 1977.
*Biochimica et Biophysica Acta*, 343 (1974), 324–329.
Proceedings of the Society for Experimental Biology and Medicine, 146, 504–508 (1974).

*Primary Examiner*—Frederick E. Waddell
*Attorney, Agent, or Firm*—Kevin M. Foley

[57] ABSTRACT

A oligo-heteropolysaccharide is disclosed which is very active against thrombotic syndromes and is prepared starting from depolymerized heparin fractions wherein the active groups, more particularly the sulfuric groups have been reconstituted by reacting a heparin fraction with a mol wt from 2,000 to 5,000 with the sulfotrioxide of a nitrogeneous organic base such as pyridine and trimethylamine. The method of preparation is also disclosed.

3 Claims, No Drawings

OLIGO-HETEROPOLYSACCHARIDES HAVING A HEPARIN-LIKE ACTIVITY METHOD FOR THEIR PREPARATION AND PHARMACEUTICAL COMPOSITIONS BASED THEREON

This is a continuation application of Ser. No. 347,026 filed on Feb. 8, 1982, now abandoned, whichis a continuation of application Ser. No. 931,295 filed Aug. 4, 1978, now abandoned.

This invention relates to a hetero-polysaccharide which is susceptible of finding a therapeutical application, in general, in the prevention of thrombotic phenomena.

Another object of the present invention is to provide a method for the preparation of such a hetero-polysaccharide.

Yet another object of the present invention is to indicate therapeutic uses and pharmaceutical compositions which contain as the active ingredient the oligo-heteropolysaccharide of the present invention.

Thrombosis is one of the most frequent factors of casualties and ailments, these latter often showing a permanent invalidity pattern in the field of the cardiovascular ailments.

The general term "thrombosis" may include conditions displaying an exalted tendency to blood-clotting, the origins of which can be attributed to:

"hazardous factors" originating a thrombogenic state, such as tobacco smoke, the stresses, the prolonged use of contraceptives of the progestogen type and others, hereditary factors, such as the lack of blood-clotting-inhibiting factors, more particularly antithrombin III, causative factors of various origin, sometimes not yet elucidated, such as modification of the platelet adhesiveness and others, factors deriving from a temporary slowing down of the blood circulation such as is experienced subsequently to surgical operations under narcosis.

The pathological after-effects consequential to a "thrombogenic" condition as caused by one or more of the factors enumerated above can be:

pulmonary, cerebral, coronaric and other thromboembolism, thrombosis of the deep-lying veins, thromboplebites, varicose syndromes, diffuse scattering of intravascular microthrombi.

Before so imposing a number of phenomena, it is possible, at present, to have recourse to two approaches:

1. The use of thrombolytic agents,
2. The preventative therapy of thrombogenic conditions and their after-effects. On account of the seriousness and the rapidity of the possible evolution of thromboses, it is apparent that, of the two approaches, the second one is to be preferred by far.

In order to face the thrombosis problem from the preventative angle, two classes of medicaments are now available, viz. the oral anticoagulants such as coumarin and its derivatives and heparin.

Oral anticoagulants such as coumarin and its derivatives act at the liver level and block the two blood-clotting factors proconvertin and prothrombin, but give rise to cumulative phenomena and thus lends themselves poorly to a prolonged treatment and, moreover, even though they are anticoagulants, have but a poor antithrombotic activity since they have no action on other blood-clotting factors which are closely involved in the thromobogenesis, the Xa factor and the platelet factors above all.

Heparin, under this respect, yet offers advantages in that it acts upon the several plasmatic factors of blood-clotting and especially upon thrombin, the factor Xa and also on the XII factor, the XI factor and the IX factor in addition to the platelet factor called PF4. All of these actions are to be attributed to the specific ability by thrombin to unblock the inhibitor of the blood-clotting factors enumerated above, said inhibitor being present in the plasma. This inhibitor is the antithrombin III and requires, just as a co-factor to unfold its action, the presence of heparin.

Regrettably enough, heparin has two defects: in the first place, it is active only parenterally and its effect lasts for 8–12 hours as a maximum, so that it is difficult to bring about a prolonged prophylaxis, for which 2 heparin shots daily are required. In the second place, heparin has not only an antithrombotic effect but also an anti-blood-clotting action as a whole. Now, if this second effect is an asset in certain instances, in other cases the haemorrhage hazard, if the therapy is not adapted to the individual patient, becomes a serious trouble even if the prophylaxix of thrombosis offers advantages beyond any doubt.

Low mol. wt. heparin fractions are found in two cases:

(a) when depolymerizing heparin which chemical or enzymic methods (cfr. A. Horner, in "HEPARIN", Kakkar, Thomas, 1976 and Perhin and cow., Carb. Res., 18, 185 (1971)).

(b) in the mother liquors of the processes for extracting heparin for therapeutical use.

Such fractions, having a mol wt of 5,000 and containing variable amounts of sulfuric groups, generally less numerous than in heparin, have not found any useful therapeutic application heretofore.

It has now been found that such fractions, should they contain the sulfuric groups in the quantities and the positions which are characteristic of the heparin molecule, have pharmacological properties which are akin to those of heparin and therapeutical properties even improved over those of heparin. More particularly, it has been ascertained that:

(i) oligopolysaccharide fractions coming from the depolymerization of heparin, or corresponding to depolymerized heparins having a mol wt comprised between 2,000 and 5,000 have biopharmacological properties which are improved over those of heparin, providing that they are appropriately treated so as to rebuild the active groups;

(ii) differently from heparin as such, the thus treated fractions are active also by the oral route;

(iii) the fractions thus treated are more readily absorbed by the skin than is heparin;

(iv) more particularly, depolymerized and reconstituted heparins are endowed with a ratio of the antithrombotic activity to the anti-blood-clotting activity which is favourable over that of the commercial heparin.

The method according to the present invention can be summarized as follows: the starting material is selected from among the heparin oligomers having a mol wt comprised between 2,000 and 5,000 and the low mol wt fractions and is treated with an equal amount by wt of sulfotrioxides of nitrogenous organic bases such as pyridine sulfotrioxide, trimethylamine sulfotrioxide and other in an alkaline environment.

On completion of the reaction, the product is precipitated with water-miscible solvents such as ethanol, acetone and others and is taken up in an aqueous solution and purified by flowing through ion-exchange resins or molecular sieves.

From the solution the product is obtained by precipitation with water-miscible solvents or by freeze-drying.

The product thus obtained has the following properties:

Identification:
an ivory-colored powder which is slightly hydroscopic, aqueous solution which is clear or slightly opalescent,
pH of the 5% aqueous solution: 7 to 8,
identification metachromatic reaction: 1 ml of a 2% solution of the product, added to 1 ml of a 0.0025% toluidine blue solution acidified with 0.1 ml of 1-N hydrochloric acid discharges the color from blue to reddish-blue,
specific rotatory power of the aqueous solution $[\alpha]_D^{20} = +40°/+50°$,
electrophoresis on cellulose acetate pyridine/acetic acid/water-1/10/229, pH 4.5 and development with toluidine blue) = a single band having an anodic mobility $U = 2.1 \cdot 10^{-4} \, cm^2 \, v^{-1} \, sec^{-1}$.

Other chemical specifications of the invention are:

Average mol wt (determined with the Somogy method in comparison with commercial heparin): between 2,600 and 5,500 daltons.
Hexosamines after hydrolysis (reaction with carbazol): 31±4%,
Organic $SO_4^{--}$ after hydrolysis (titration with naphtharsone): 30±4%,
Molar ratio uronic acids/hexosamines/$SO_4^{--}$ = 1/1/2.

The following Examples show particularly the method of preparation of the products according to the invention without any limitation.

EXAMPLE 1

500 g of an oligopolysaccharide having the following fundamental analytical characteristics:
pH of the 5% solution: 5.8
Organic $SO_4^{--}$: 13.6%
rotatory power $[\alpha]_D^{20} = +48°$
mol wt (determined with the Somogy method in comparison with commercial heparin = 4,850±300 daltons,
Hexosamines: 33.5%
Uronic acids: 31.8%

Anticoagulant activity: virtually nil, have been admixed in powder with 500 g of Pyridine sulfotrioxide and 500 g of anh. sodium carbonate.

The mixture has been slurried in 10 liters of distilled water and kept stirred for 2 hrs. at room temperature.

Once that time has elapsed, the liquid has been treated with 20 liters of methanol. A white precipitate has been formed, which, separated by centrifuging, has been redissolved in 5 liters of distilled water and passed through a column (diameter 16 cm. height 110 cm) containing 20 liters of Dowex Retardion 11 A 8.

The eluate has been adjusted to a pH of 6 with 20% sodium hydroxide and treated with 2 volumes of methanol. Upon decantation, the white precipitate has been dehydrated with methanol and dried in a vacuum at 40° C. Yield: 365 g.

The product has displayed the following properties upon analysis:

pH of the 5% solution: 6.5
Organic $SO_4^{--}$: 31%
rotatory power: $[\alpha]_D^{20}: +47°$
mol wt (determined with the Somogy method in comparison with commercial heparin: 5,300±350 daltons
hexosamines: 28.5%
uronic acids: 30%
anticoagulant activity: 36 U/gm (USP)

EXAMPLE 2

250 g of trimethylamine sulfotrioxide and 250 g of anh. sodium carbonate have been admixed, in powder form, with 250 g of an oligopolysaccharide having the following fundamental analytical properties:
pH of the 5% aqueous solution: 6.4
mol wt (determined with the Somogy method in comparison with commercial heparin: 3,400±400 daltons
Organic $SO_4^{--}$: 11.8%
Hexosamines: 34.2%
Uronic acids: 36%
Anticoagulant activity (USP): 0.5 U/mg The mixture has been dispersed in 5 liters of dist. water and stirred 12 hours at 55° C. After this time hs elapsed, the solution has been passed through a bed of 10 liters of Dowex Retardion 11 A 8. The eluate has been adjusted to a pH of 6 with 20% sodium hydroxide and treated with three volumes of acetone. A white precipitate has been formed which, after decantation, has been dehydrated with acetone and dried in a vacuum at 40° C. Yield: 165 g.

The product has shown the following analytical properties:
pH of the 5% aqueous solution: 7.1%
Rotatory power: $[\alpha]_D^{20} = +42°$
mol wt (determined with the Somogy method in comparison with commercial heparin: 3,900±280 daltons
Organic $SO_4^{--}$: 28.5%
Hexosamines: 29%
Uronic acids: 30%
Anticoagulant activity: 17 U/mg (USP)

The product obtained with the method described above has been subjected to assays to ascertain its pharmacobiological properties and its activity.

Toxicological tests:
No toxic effects when administered orally to rats, mice, rabbits and Guinea pigs up to a dose of 1,000 mg/kg b.w.
$LD_{50}$ i.p. (mice) more than 3,000 mg/kg b.w.: $LD_{50}$ i.v. (mice): more than 1,000 mg/kg b.w.
$LD_{50}$ i.p. (rats) about 2,000 mg/kg b.w. $LD_{50}$ i.v. (rats) 354 mg/kg b.w.

Clarifying activity test:
The product lowers the seral levels of the triglycerides considerably in animals affected by experimental hyperlipaemia from Triton.

Anticoagulant activity:
USP equal to, or more than 50 U/mg
Kaolin-Cephalin clotting time test (KCCT): 7-19
Ratio of antithrombotic activity to anticoagulant activity in vitro (Yin's/KCCT): 2.5.

In vivo (dogs) antithrombotic and anticoagulant activity.

The product, administered intravenously (i.v.) (25 IU/kg) and orally (300–1500 U/kg) extends the thrombine time and the KCCT, and protects against thrombosis as induced by thromboplastines.

In vivo (rabbits) antithrombotic activity.

The product administered intravenously at the dose of 20 Anti Xa U/kg protects from thrombine-induced thrombosis.

Thus, the following predictable therapeutic uses are suggested, either orally or parenterally:

prevention of post-operatory thromboembolisms prevention of thrombotic seizures consequent to a thrombogenic conditions such as for example that which occurs in fertile women when treated for a long time with oral contraceptives of progestogenic type prevention of venous thromboses prevention of hypercoagulability states correction of the hyperdislipaemic states (hyperdislipoproteinaemias).

We claim:

1. A method of increasing the antithrombotic activity of mammalian blood relative to the anticoagulant activity comprising administering to a mammal in need of treatment for thrombosis, an oligoheteropolysaccharide comprising depolymerized heparin containing sulfate groups in the quantity and in the positions characteristic of heparin wherein said oligoheteropolysaccharide has the following physico chemical properties:
   (A) average molecular weight (determined with the Somogy method in comparison with commercial heparin) from 2600 to 5500 daltons;
   (B) hexosamines after hydrolysis (reaction with p-dimethyl-amino benzaldehyde): 28% ±2%;
   (C) uronic acids after hydrolysis (reaction with carbazol): 31% ±4%;
   (D) organic $SO_4^=$ after hydrolysis (titration with naphtharsone): 30% ±4%;
   (E) molar ratios of uronic acids/hexosamines/$SO_4^=$ = 1/1/2;
   (F) specific rotatory power of the aqueous solution $[\alpha]_D^{20} = +40° - +50°$;
   (G) electrophoresis on cellulose acetate (pyridine/acetic acid/water (1:10:299)) pH 4.5 and development with toluidine blue=a single band with anodic mobility $U = 2.1 \times 10^{-4} \text{ cm}^2 \text{v}^{-1} \text{sec}^{-1}$;
   (H) powder of ivory color, amorphous and slightly hygroscopic;
   (I) aqueous solution clear or slightly opalescent; and
   (J) pH of 5% aqueous solution: 7–8.

2. A method of increasing the antithrombotic activity of mallalian blood relative to the anticoagulant activity comprising administering to a mammal in need of treatment for thrombosis an oligoheteropolysaccharide comprising depolymerized heparin having an average molecular weight of about 2600 to about 5500 daltons determined by the Somogy method in comparison with commercial heparin and having sulfate groups in the quantity and in the positions characteristic of heparin, which oligoheteropolysaccharide displays greater antithrombotic activity than anticoagulant activity.

3. A method of increasing the antithrombotic activity of mammalian blood relative to the anticoagulant activity comprising administering to a mammal an effective amount of a therapeutical composition, for the prevention of thrombosis, characterized in that it contains as the active ingredient the oligoheteropolysaccharide as described in claims 1 or 2.

* * * * *